United States Patent
Fumuro et al.

(10) Patent No.: US 7,122,009 B2
(45) Date of Patent: Oct. 17, 2006

(54) SPHYGMOMANOMETER AND SPHYGMOMANOMETER STORAGE CASE

(75) Inventors: Shinichi Fumuro, Hikone (JP); Koichi Okada, Hikone (JP); Tsuyoshi Yuasa, Hikone (JP)

(73) Assignee: Matsushita Electric Works, Ltd., Osaka (JP)

( * ) Notice: Subject to any disclaimer, the term of this patent is extended or adjusted under 35 U.S.C. 154(b) by 0 days.

(21) Appl. No.: 10/410,501

(22) Filed: Apr. 8, 2003

(65) Prior Publication Data

US 2003/0220575 A1 Nov. 27, 2003

(30) Foreign Application Priority Data

Apr. 10, 2002 (JP) ............................. 2002-107817

(51) Int. Cl.
*A61B 5/02* (2006.01)
(52) U.S. Cl. ...................... 600/499; 600/490
(58) Field of Classification Search ............... 600/485, 600/490, 500–503
See application file for complete search history.

(56) References Cited

U.S. PATENT DOCUMENTS

| | | | | |
|---|---|---|---|---|
| 4,549,550 A | | 10/1985 | Kami ........................ 128/686 |
| 5,002,061 A | * | 3/1991 | Close et al. ................ 600/490 |
| 5,406,953 A | * | 4/1995 | Bui ............................ 600/490 |
| 5,687,732 A | * | 11/1997 | Inagaki et al. .............. 600/485 |
| 5,807,266 A | * | 9/1998 | Itonaga et al. ............... 600/499 |
| 6,251,080 B1 | | 6/2001 | Henkin et al. ............... 600/490 |
| 6,344,025 B1 | | 2/2002 | Inagaki et al. ............... 600/490 |
| 6,443,905 B1 | * | 9/2002 | Nissila et al. ............... 600/490 |
| 2002/0095091 A1 | * | 7/2002 | Che et al. .................... 600/490 |

FOREIGN PATENT DOCUMENTS

EP 1 010 392 A1 6/2000

OTHER PUBLICATIONS

European Search Report dated Oct. 15, 2003, 5 pages.

* cited by examiner

*Primary Examiner*—Robert L. Nasser
(74) *Attorney, Agent, or Firm*—Osha Liang LLP

(57) ABSTRACT

To facilitate carrying by making a sphygmomanometer combining a blood-constricting cuff band with a sphygmomanometer unit thin and compact when not engaged in measurement, a sphygmomanometer combines blood-constricting cuff band 1 with sphygmomanometer unit 2, and constitutes a structure that can be switched between measurement position (I) with sphygmomanometer unit 2 overlapping blood-constricting cuff band 1 and storage position (II) with blood-constricting cuff band 1 and sphygmomanometer unit 2 placed side by side.

13 Claims, 17 Drawing Sheets 1 blood-constricting cuff band
2 sphygmomanometer unit
3 connecting base
4 unit case 1 blood-constricting cuff band
2 sphygmomanometer unit
3 connecting base
4 unit case

SPHYGMOMANOMETER AND SPHYGMOMANOMETER STORAGE CASE

CROSS-REFERENCE TO RELATED APPLICATIONS

This application claims priority from Japanese Patent Application No. 2002-107817 filed Apr. 10, 2002.

BACKGROUND OF INVENTION

1. Field of the Invention

This invention pertains to a sphygmomanometer and a sphygmomanometer storage case. More particularly, this invention pertains to technology for facilitating carrying and the like by making a sphygmomanometer combining a blood-constricting cuff band with a sphygmomanometer unit thin and compact when not engaged in measurement.

2. Background Art

In conventional sphygmomanometers combining a blood-constricting cuff band with a sphygmomanometer unit, air is fed under pressure from a pump installed on the sphygmomanometer unit to the blood-constricting cuff band, and air in the blood-constricting cuff band is expelled from an air release valve installed on the sphygmomanometer unit. For this purpose, the blood-constricting cuff band is fixed to the sphygmomanometer unit by means such as screws or hooks.

The sphygmomanometers combining the blood-constricting cuff band with the sphygmomanometer unit, however, have the problem that they are difficult to make thin and cannot be made compact because of the overlapping thickness of the two parts, making them unwieldy to carry and ill-suited for portability.

SUMMARY OF INVENTION

In one or more embodiments, the invention is a sphygmomanometer combining a blood-constricting cuff band 1 with a sphygmomanometer unit 2, comprising a structure that can be switched between a measurement position (I) with the sphygmomanometer unit 2 overlapping the blood-constricting cuff band 1, and a storage position (II) with the blood-constricting cuff band 1 and the sphygmomanometer unit 2 placed side by side. According to such a constitution, the sphygmomanometer can be switched to the storage position (II) with the blood-constricting cuff band 1 and the sphygmomanometer unit 2 placed side by side, and the sphygmomanometer combining the blood-constricting cuff band 1 with the sphygmomanometer unit 2 can be made compact, facilitating carrying and the like.

In one or more embodiments, the invention is characterized by pivoting the blood-constricting cuff band 1 freely rotating on a pivot shaft 5 of a unit case 4 of the sphygmomanometer unit 2, and also comprising the pivot shaft 5 as an air pipe for supplying and expelling air from the sphygmomanometer unit 2 to the blood-constricting cuff band 1. According to such a constitution, the blood-constricting cuff band 1 can be placed side by side with the sphygmomanometer unit 2 by rotating the blood-constricting cuff band 1 on the pivot shaft 5. In addition, regardless of making the sphygmomanometer even thinner, because the pivot shaft 5 also functions as an air pipe, the air supply system can be simplified rather than complicated.

In one or more embodiments, the invention is characterized by having an air supply/stop module 6 for enabling air supply from the sphygmomanometer unit 2 to the blood-constricting cuff band 1 when in the measurement position (I) and disabling air supply from the sphygmomanometer unit 2 to the blood-constricting cuff band 1 when in the storage position (II). According to such a constitution, the blood-constricting cuff band 1 cannot be supplied air by the air supply/stop module 6 when it is in the storage position (II), preventing it from operating when not engaged in measurement.

In one or more embodiments, the invention comprises the blood-constricting cuff band 1 sliding freely against the sphygmomanometer unit 2. According to such a constitution, the constitution for placing the blood-constricting cuff band 1 in the storage position (II) can be easily simplified compared to a rotating constitution.

In one or more embodiments, the invention is characterized by having an expansion prevention module 7 for preventing the blood-constricting cuff band 1 from expanding in the storage position (II). According to such a constitution, the blood-constricting cuff band 1 can be prevented from expanding by the expansion prevention module 7, and the sphygmomanometer can be made even thinner.

In one or more embodiments, the invention is characterized by holding the blood-constricting cuff band 1 on the connecting base 3 of a hard substance, and pivoting the connecting base 3 on the unit case 4 of the sphygmomanometer unit 2. According to such a constitution, the blood-constricting cuff band 1 can be switched between the measurement position (I) and the storage position (II) and held stably in each position (I) and (II) by way of the connecting base 3 of a hard substance.

In one or more embodiments, the invention is characterized by forming a tube 19 open on both ends on the side of the connecting base 3 toward the unit case 4, extending a connecting pipes 22 perpendicular to the axial center of the tubular pivot shafts 5 inserted into both ends of the tube 19, closing one end of each tubular pivot shaft 5, forming a polygonal shaft 23 having parallel faces 23a, 23a on this closed end, forming a square bearing 24 for bearing parallel faces 23a, 23a of a polygonal shaft 23 on the unit case 4 to hold the pivot shaft 5 and stop it from rotating, connecting the tubular pivot shafts 5, 5 freely rotating in the tube 19 by inserting the pivot shafts 5 through an O-rings 20 onto both ends of the tube 19, and connecting the air pipe 26 from a pump 25 to the connecting pipe 22 of the pivot shaft 5. According to such a constitution, the shafts can be sealed by O-rings 20, the polygonal shafts 23 of the pivot shafts 5 can be inserted in the square bearings 24 and prevented from rotating, the pivot shafts 5 can be held securely while facilitating assembly of the pivot shafts 5 with the unit case 4, and rotation of the connecting base 3 can be stabilized. Moreover, because the polygonal shaft 23 has parallel faces 23a, 23a, different rotating angles can be selected for the polygonal shafts 23 and the different directions can be selected for the connecting pipes 22 extending from the pivot shafts 5, producing a variety of potential placements for parts of the sphygmomanometer unit 2 such as the pump 25.

In one or more embodiments, the invention is characterized by forming a hook 10 on either the unit case 4 or the connecting base 3, and forming a hook catch 11 on the other one for the catching hook 10 to hold the blood-constricting cuff band 1 in the measurement position (I). According to such a constitution, the connecting base 3 can be fixed to the unit case 4 and the blood-constricting cuff band 1 can be held stably in measurement position (I) by locking the hook 10 by the hook catch 11.

In one or more embodiments, the invention is characterized by forming a battery storage space 8 on the connecting base 3. According to such a constitution, the battery storage space 8 need not be installed on the sphygmomanometer unit 2, simplifying the constitution of the sphygmomanometer unit 2.

In one or more embodiments, the invention is characterized by installing a switch 12 for switching the power source battery off only when the blood-constricting cuff band 1 is in the storage position (II). According to such a constitution, the switch 12 cannot be switched on when the blood-constricting cuff band 1 is in the storage position (II), preventing unexpected consumption of power.

In one or more embodiments, the invention is characterized by installing the switch 12 for switching the power source on only when the blood-constricting cuff band 1 is in the measurement position (I). According to such a constitution, the switch 12 cannot be switched on except when the blood-constricting cuff band 1 is in the measurement position (I), preventing unexpected consumption of power.

In one or more embodiments, the invention is a storage case for storing the sphygmomanometer in the storage position (II), characterized in having a presser member 13 for preventing the blood-constricting cuff band 1 from expanding. According to such a constitution, the blood-constricting cuff band 1 is pressed by the presser member 13 in the storage position (II) and prevented from expanding when the sphygmomanometer A is stored in a storage case 27, making the storage case 27 thin.

In one or more embodiments, the invention is characterized by installing a latching hook 14 on the outside of the case for latching to clothing or the like. According to such a constitution, the storage case 27 can be easily carried by latching the latching hook 14 to a pocket or belt.

In one or more embodiments, the invention is characterized by installing a support leg 15 standing at an angle to the storage case 27 freely rotating on the outside of the case. According to such a constitution, the storage case 27 can be raised at an angle by standing the support leg 15 up, enabling stable measurement of blood pressure with the wrist raised to roughly the height of the heart.

In one or more embodiments, the invention is characterized by forming a small hole 17 for depressing and operating a switch 16 on the sphygmomanometer when stored. According to such a constitution, the switch 16 such as a time setting switch installed on the sphygmomanometer unit 2 can be operated externally through the small hole 17.

In one or more embodiments, the invention is characterized by having a module 18 for balancing the weight of the blood-constricting cuff band 1 and the sphygmomanometer unit 2 of the sphygmomanometer on either side of case center-line C when stored. According to such a constitution, the sphygmomanometer can be stabilized when carried, preventing dropping.

DETAILED DESCRIPTION

Figure 1A:
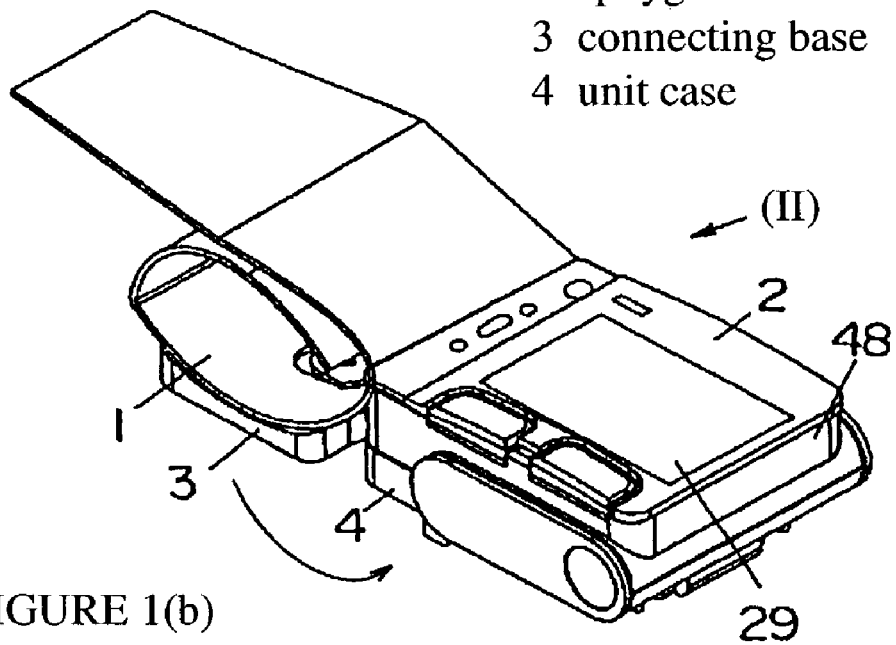
FIG. 1 is a diagram showing an embodiment of this invention, where (a) is an oblique perspective diagram of a blood-constricting cuff band in storage position and (b) is an oblique perspective diagram in measurement position.
Figure 1B:
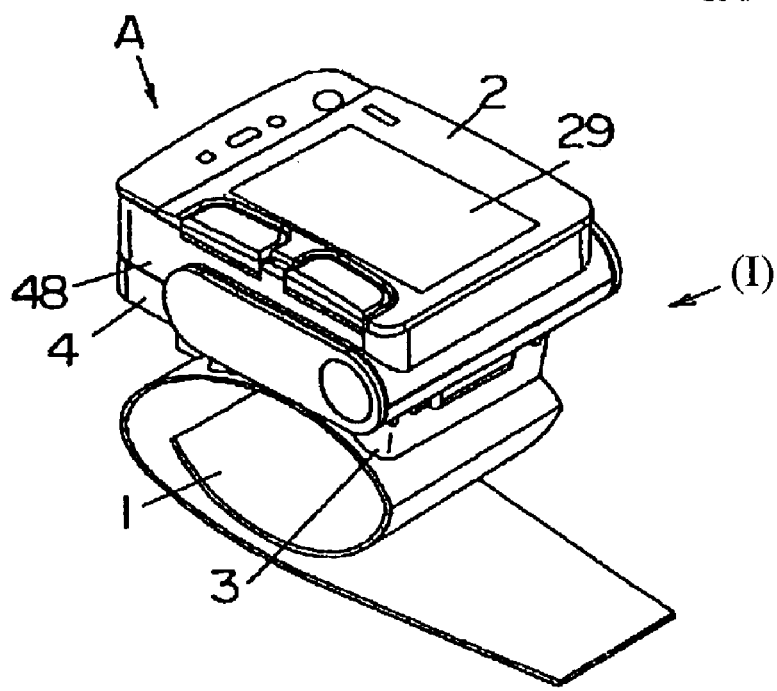
Figure 2A:
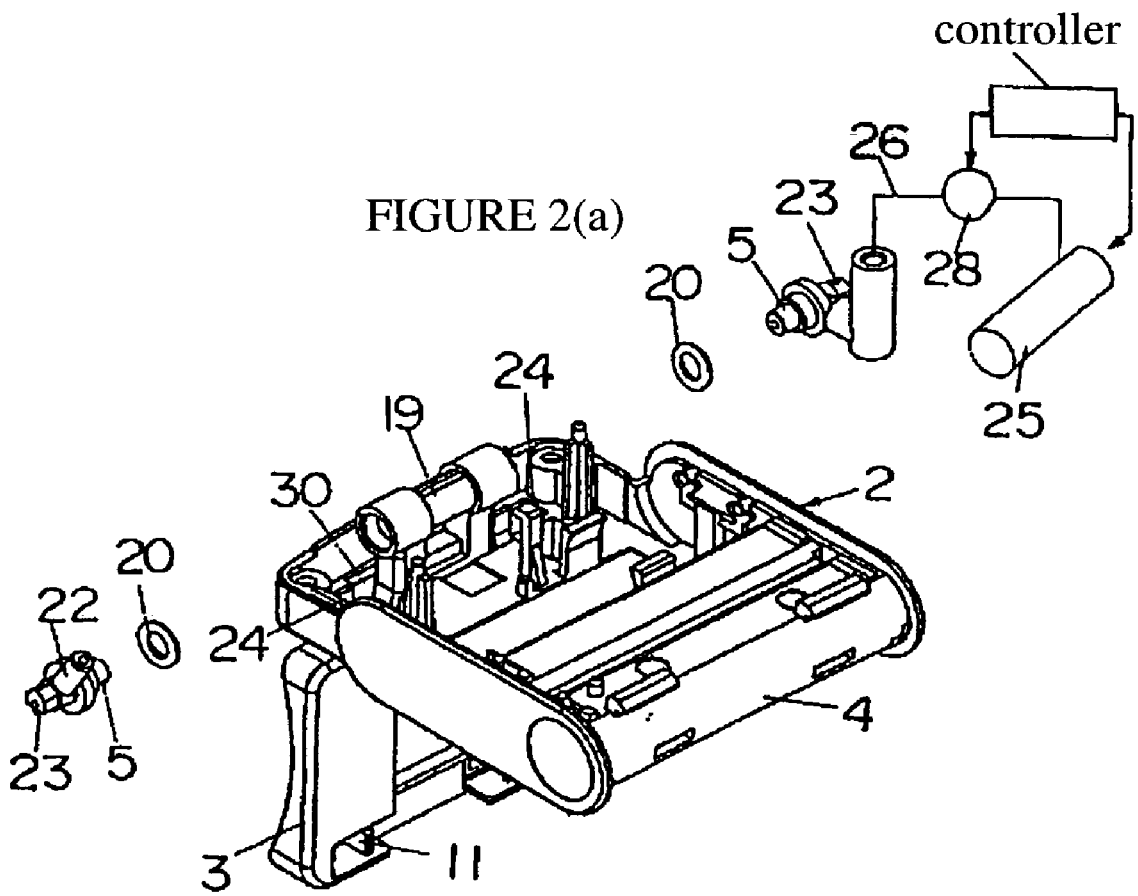
FIG. 2 is a diagram showing the configuration of the pivot connection between the unit case and the connecting base in the same, where (a) is a partially exploded oblique perspective diagram and (b) is a schematic diagram.
Figure 2B:
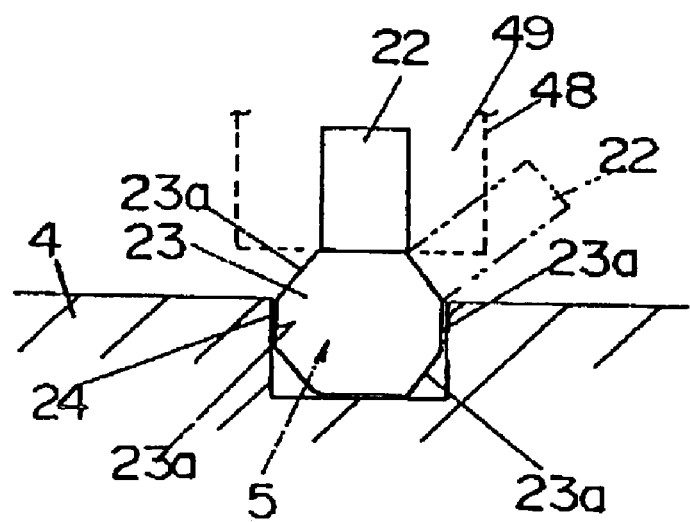
Figure 3:
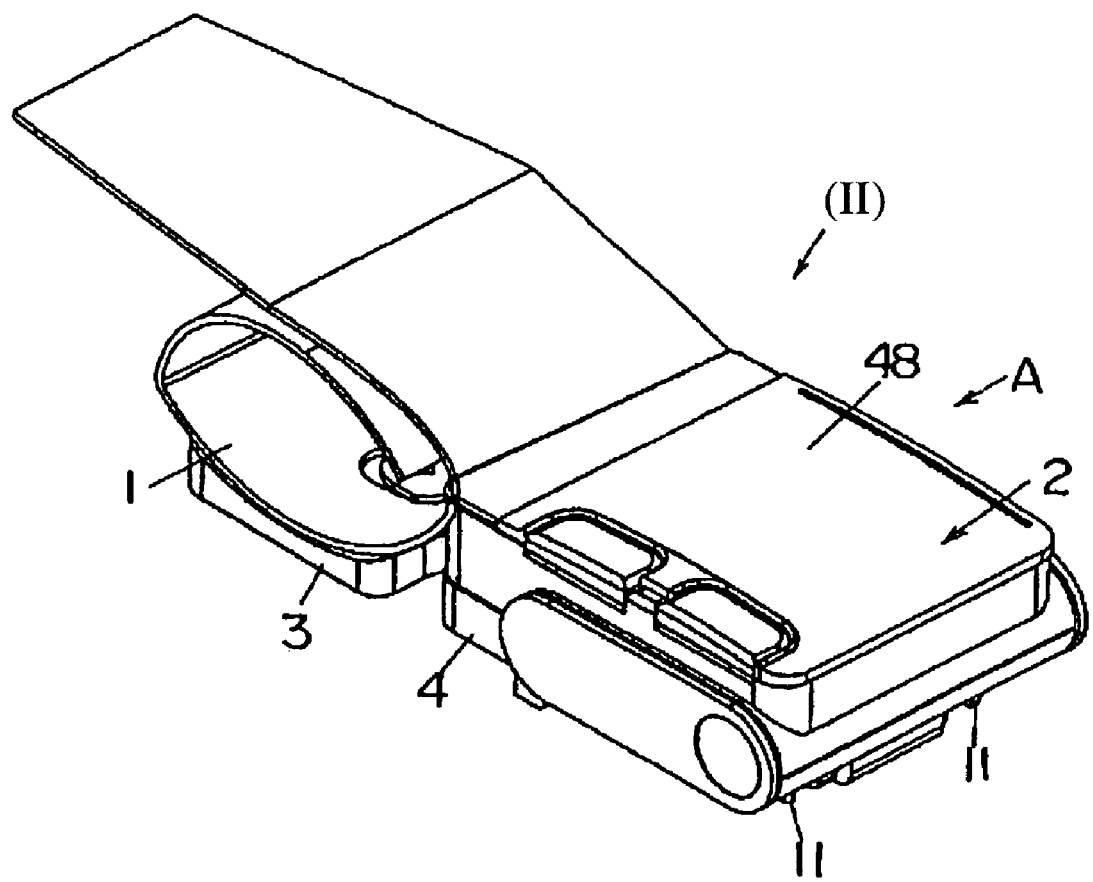
FIG. 3 is a perspective diagram of the same in storage position.

The preferred embodiment of this invention will be explained below. FIG. 1($a$) is a perspective diagram of a blood-constricting cuff band in storage position, and FIG. 1($b$) is an oblique perspective diagram in measurement position. FIG. 2 shows the configuration of the pivot connection between the unit case and a connecting base, where FIG. 2($a$) is a partially exploded oblique perspective diagram and FIG. 2($b$) is a schematic diagram. FIG. 3 is an oblique perspective diagram in the storage position.

A sphygmomanometer A combines the blood-constricting cuff band 1 with the sphygmomanometer unit 2. The sphygmomanometer A constitutes a structure that can be switched between measurement position (I) with the sphygmomanometer unit 2 overlapping the blood-constricting cuff band 1 and storage position (II) with the blood-constricting cuff band 1 and the sphygmomanometer unit 2 placed side by side, enabling the combined sphygmomanometer A to be thin and compact and facilitating portability. The description will be explained in detail below.

The sphygmomanometer unit 2 houses parts such as a pump 25, a selector valve 28, a controller, and a power source battery inside a resin-molded unit case 4. The sphygmomanometer unit 2 supplies air from the pump 25 to the blood-constricting cuff band 1 wrapped around the wrist based on operations on the operational panel, measures the lowest and highest blood pressures, and displays in a display window 29. After measuring, the sphygmomanometer expels air from the blood-constricting cuff band 1, and then the sphygmomanometer unit 2 is placed in measurement wait state.

As shown in FIG. 2, a through-hole 30 is formed in the unit case 4, and the tube 19, which is formed on the edge of connecting base 3 holding the blood-constricting cuff band 1, is inserted into the through hole 30. The tube 19 freely rotating on the pivot shafts 5, 5 fixed to the unit case 4. The shape of the sphygmomanometer unit 2 can be switched between the measurement position (I) with the connecting base 3 overlapping the unit case 4 and the storage position (II) made thin by spreading the connecting base 3 roughly 180° to the unit case 4. In this way, the shape of the sphygmomanometer can be switched to the storage position (II) with the blood-constricting cuff band 1 and the sphygmomanometer unit 2 placed side by side, and combined the sphygmomanometer A can be made thin, compact, and easily carried.

The pivot shaft 5 is formed in a pipe shape. The connecting pipe 22 extends perpendicular to the axial center. One end of the pivot shaft 5 is closed and polygonal shaft 23 having the parallel faces 23a, 23a is formed on the closed end. In addition, the square bearings 24 are formed on both sides of a through-hole 30 in the unit case 4.

Therefore, rotation of the connecting base 3 can be stabilized while facilitating assembly of the pivot shaft 5 with the unit case 4 because of inserting the parallel faces 23a, 23a of the polygonal shaft 23 unable to rotate into the square bearing 24. Moreover, because the polygonal shaft 23 has the parallel faces 23a, 23a, different rotating angles can be selected for the polygonal shaft 23 and the different directions can be selected for the connecting pipe 22 extending from the pivot shaft 5, producing a variety of potential placements for parts of the sphygmomanometer unit 2 such as pump 25.

Pivot shaft 5 is also a sort of air pipes for supplying and expelling air from the sphygmomanometer unit 2 to the blood-constricting cuff band 1, simplifying rather than complicating the air supply system. Placing O-ring 20 in between when inserting the pivot shaft 5 into the tube 19 produces adequate air-tightness and prevents air leaks. The pivot shaft 5 is kept from falling out by being pressed by the presser member 49 on the upper case 48 in the unit case 4.

Furthermore, the blood-constricting cuff band 1 can be switched between the measurement position (I) and the storage position (II) and held stably in each position (I) and (II) by the holding blood-constricting cuff band 1 on the connecting base 3 of a hard substance.

Figure 5:
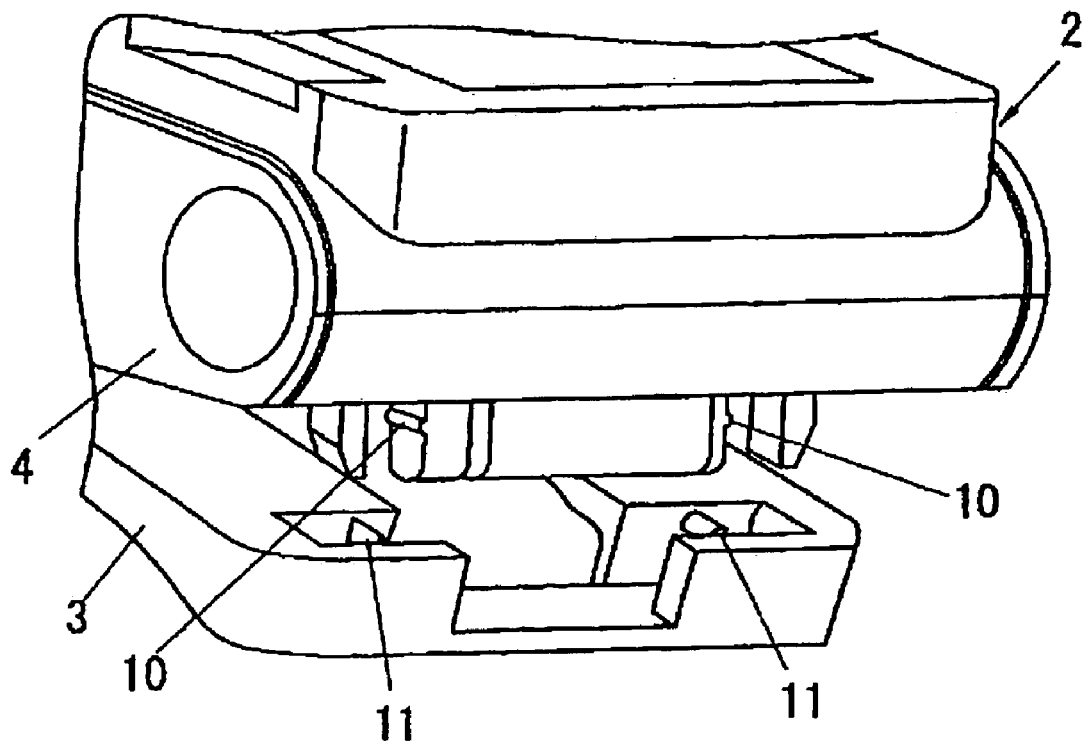
FIG. 5 is a partial perspective diagram showing the operation of the same.
Figure 6:
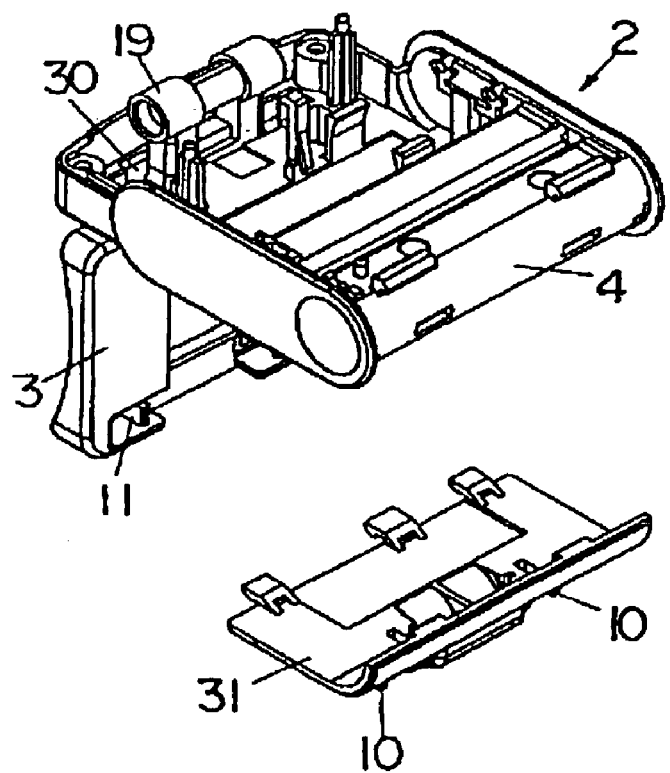
FIG. 6 is a partial perspective diagram showing the operation of the same.

The connecting base 3 can be fixed to the unit case 4 and the blood-constricting cuff band 1 can be held stably in measurement position (I), as shown in FIG. 5, by the forming hook 10 on the unit case 4, the forming hook catch 11 on the connecting base 3, and the catching hook 10 by the hook catch 11. The hook 10 is formed, for example, on the battery lid 31 installed detachably to the unit case 4 as shown in FIG. 6. It is also possible to form the hook 10 on connecting base 3 and the hook catch 11 on the unit case 4. In this way, the battery lid 31 and the connecting base 3 can be connected when placed in the measurement position (I), and the battery lid 31 can be prevented from opening in the measurement position (I).

Figure 4A:
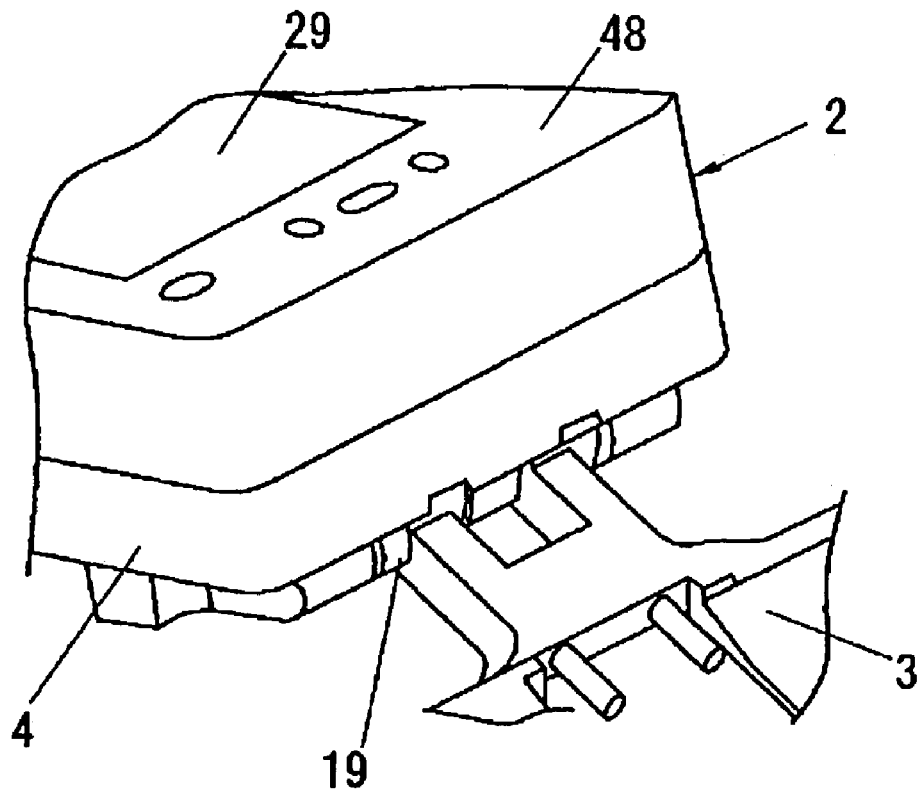
FIG. 4($a$) is a partial perspective diagram showing the operation of the same, and FIGS. 4($b$) and 4($c$) are schematic diagrams.
Figure 4B:
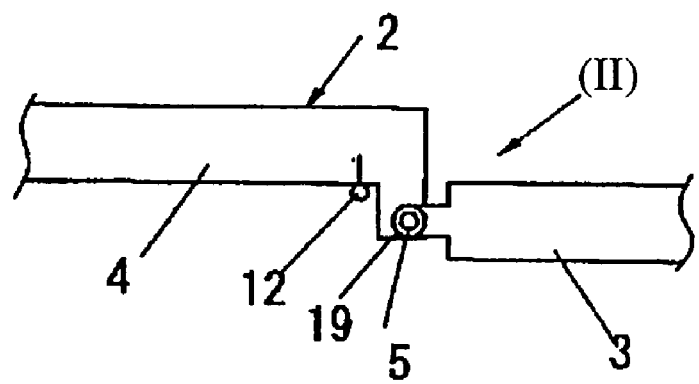
Figure 4C:
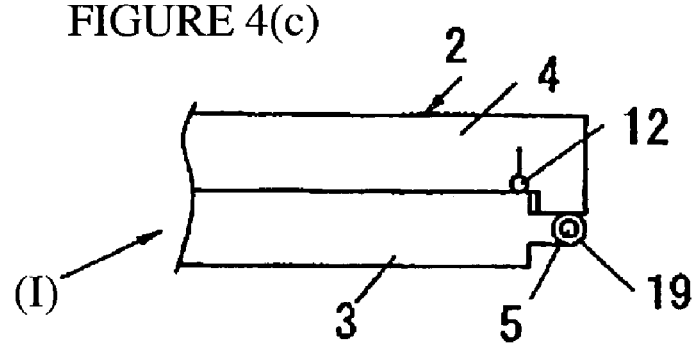

As shown in FIG. 4, the connecting base 3 is spread open roughly 180° to the unit case 4 when the blood-constricting cuff band 1 is in the storage position (II). The switch 12 is installed so that the power source battery is switched off based on using the motion of the connecting base 3. This switch 12 cannot be switched on except when the blood-constricting cuff band 1 is in the measurement position (I), preventing unexpected consumption of the power source battery. The shape of the switch 12 and the installation and configuration of the switch 12 can be modified in various ways.

Figure 7A:
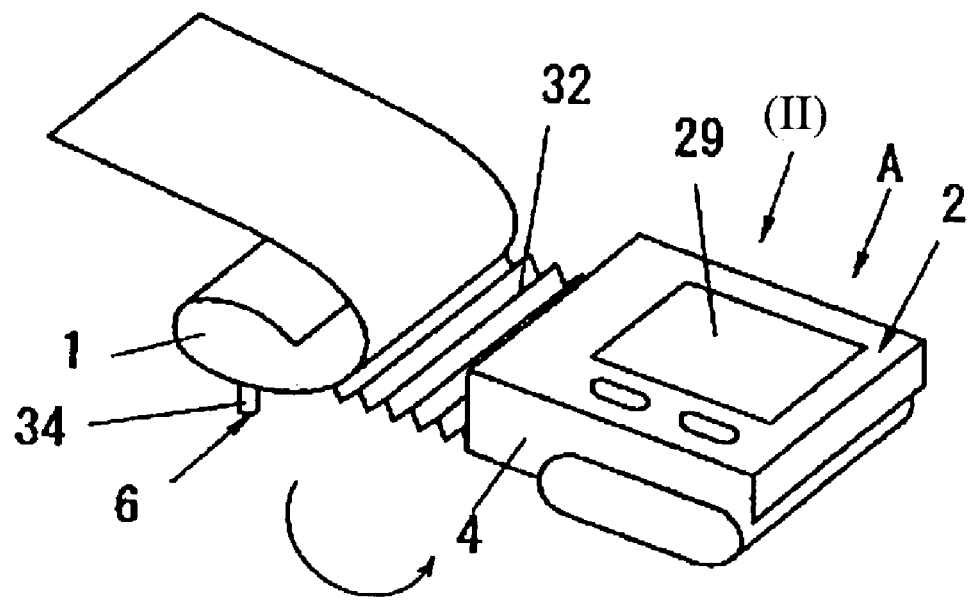
FIG. 7 is a diagram showing another embodiment of the same, where (a) is a perspective diagram and (b) is a floor elevation.
Figure 7B:
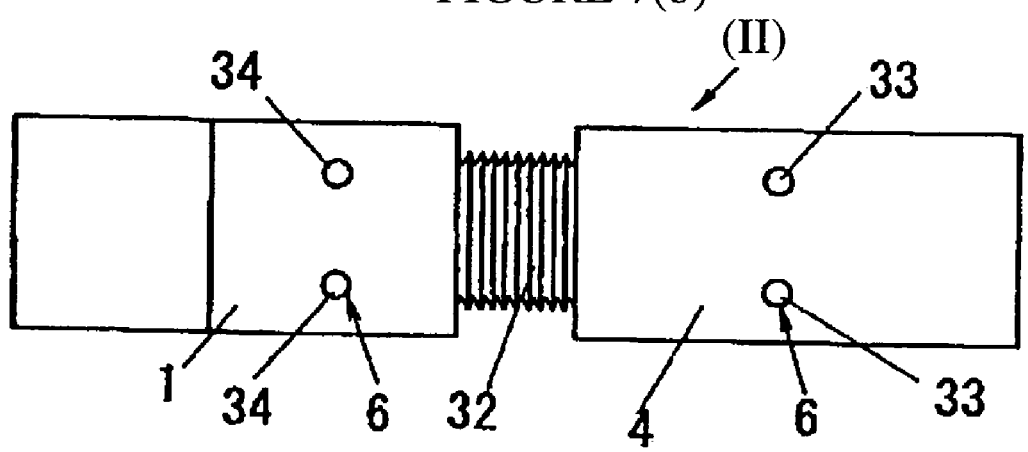

FIG. 7 shows still another embodiment. The basic constitution of this embodiment is the same as the embodiment described above, and common elements are labeled by the same reference numbers and their explanation is not repeated.

In this embodiment, the blood-constricting cuff band 1 is connected to the sphygmomanometer unit 2 freely rotating on a hinge 32. In this case, the connecting base 3 may be omitted from the blood-constricting cuff band 1.

As shown in FIG. 7(*b*), one or more connector depressions 33 having, for example, a check valve, which is capable of supplying and expelling air, and which is closed regularly, are formed on the sphygmomanometer unit 2. One or more connector projections 34 having, for example, a check valve, which is capable of receiving and expelling air, and which is closed regularly, are formed on the blood-constricting cuff band 1. Air is supplied and expelled by connecting the connector projections 34 with the connector depressions 33. Such a constitution, that is, enabling air supply from the sphygmomanometer unit 2 to the blood-constricting cuff band 1 when in the measurement position (I) and disabling air supply from the sphygmomanometer unit 2 to the blood-constricting cuff band 1 when in the storage position (II), is called an air supply/stop module 6.

According to such a constitution, air cannot be supplied by air supply/stop module 6 when the blood-constricting cuff band 1 is placed in the storage position (II), therefore, an unexpected operation may be prevented.

Figure 8A:
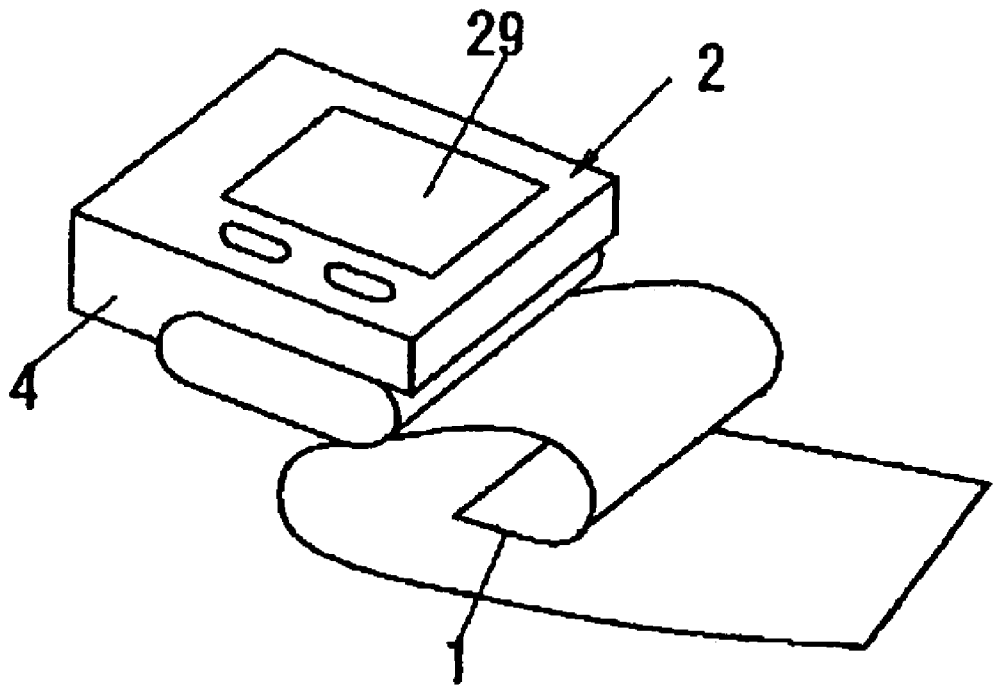
FIG. 8 is a diagram showing still another embodiment of the same, where (a) and (b) are schematic diagrams showing operation.
Figure 8B:
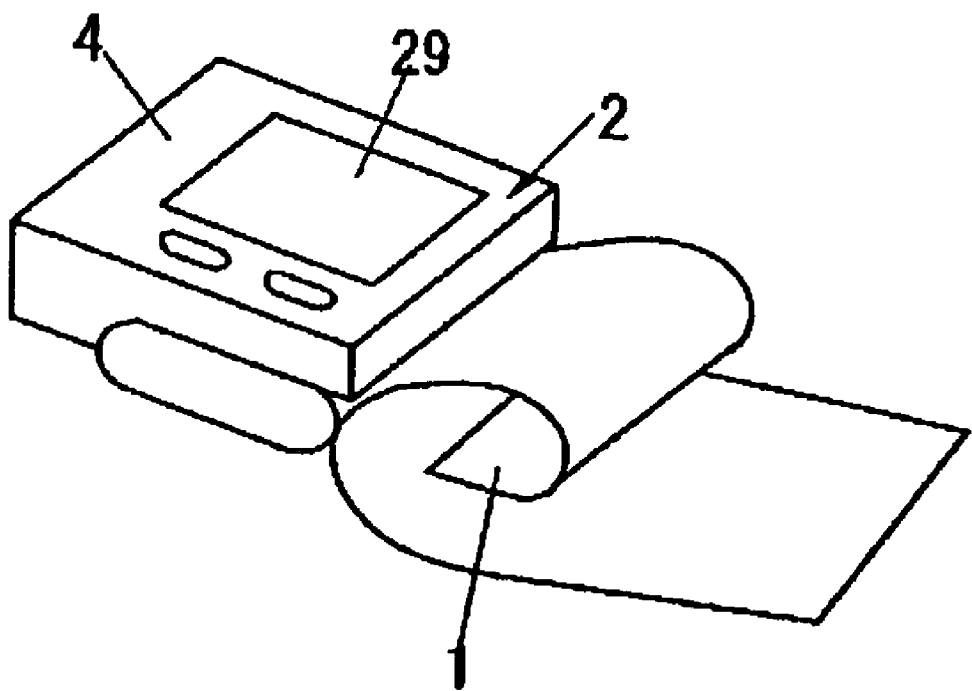
Figure 9A:
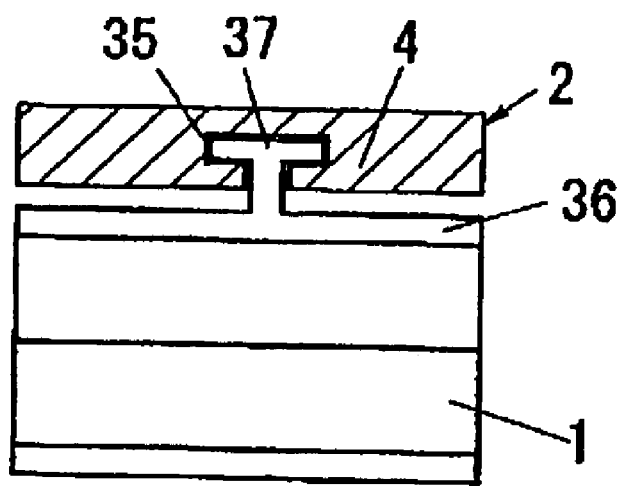
FIG. 9($a$) is a schematic section, and FIG. 9($b$) is a schematic perspective diagram.
Figure 9B:
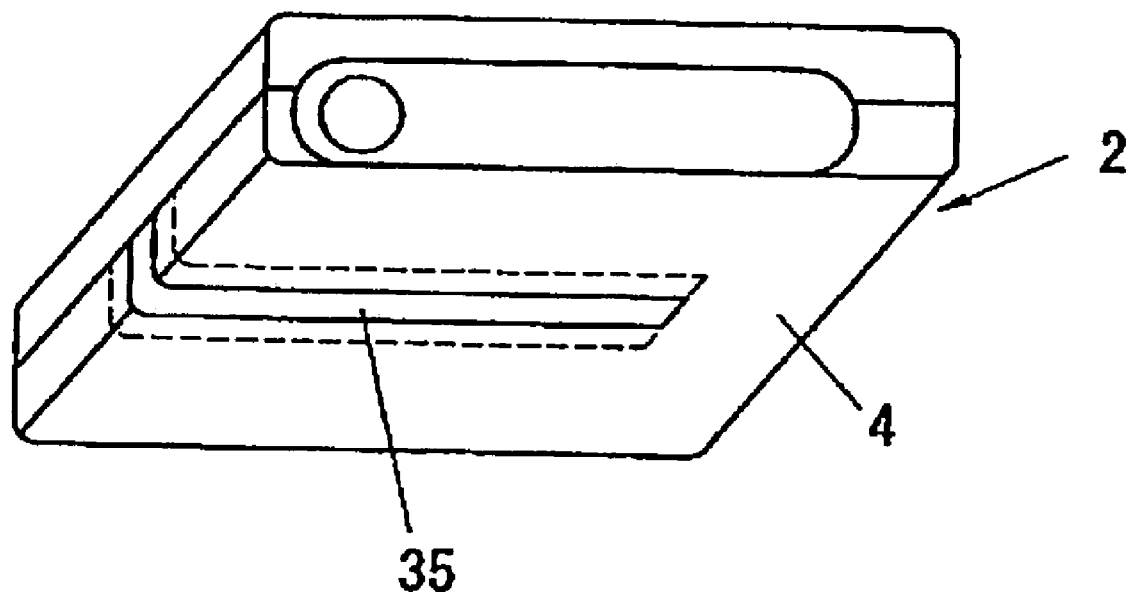

FIGS. 8 and 9 show still another embodiment. The basic constitution of this embodiment is the same as the embodiment described above, and common elements are labeled by the same reference numbers and their explanation is not repeated.

In this embodiment, the blood-constricting cuff band 1 is constituted so that it is able to switch between the measurement position (I) and the storage position (II) based on constituting the blood-constricting cuff band 1 sliding freely to the sphygmomanometer unit 2. Specifically, as shown in FIG. 9, a dovetail channel 35 is formed across the floor and side wall of the unit case 4, a slider 37 becoming larger in the section at the tip is installed on a base plate 36 of the blood-constricting cuff band 1. The slider 37 is inserted sliding freely in the dovetail channel 35, and the blood-constricting cuff band 1 slides freely to the sphygmomanometer unit 2.

This embodiment can simplify the constitution compared to constituting the blood-constricting cuff band 1 to rotate on the sphygmomanometer unit 2.

Figure 10A:
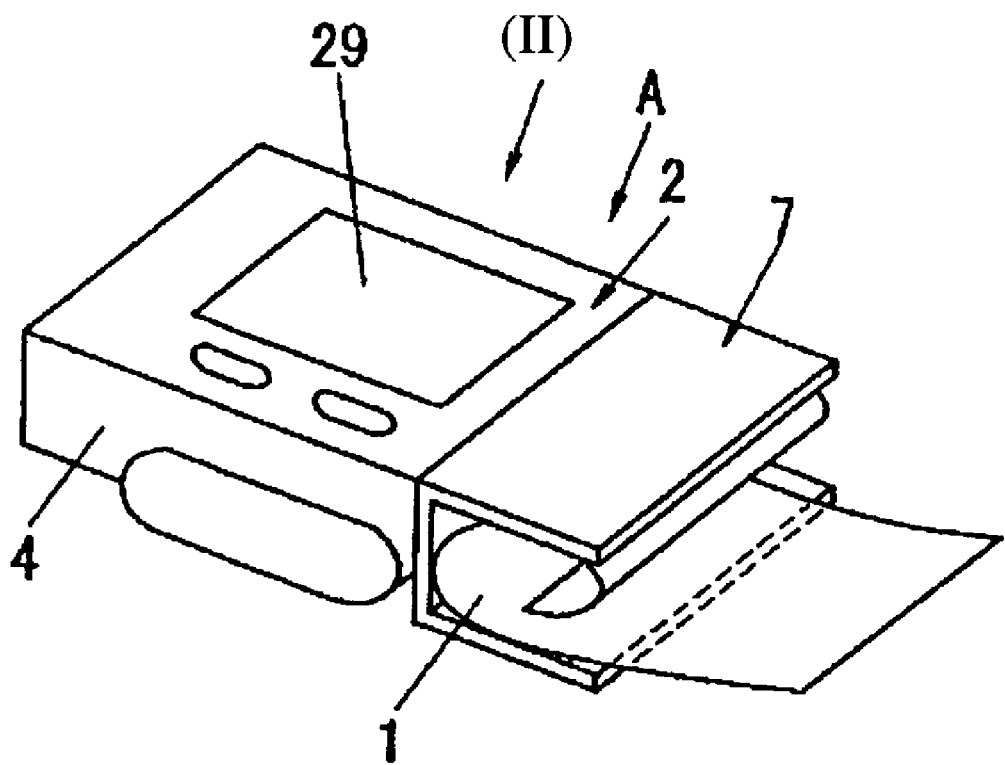
FIG. 10 is a diagram showing still another embodiment of the same, where (a) is a schematic perspective diagram and (b) is a perspective diagram of an expansion prevention module.
Figure 10B:
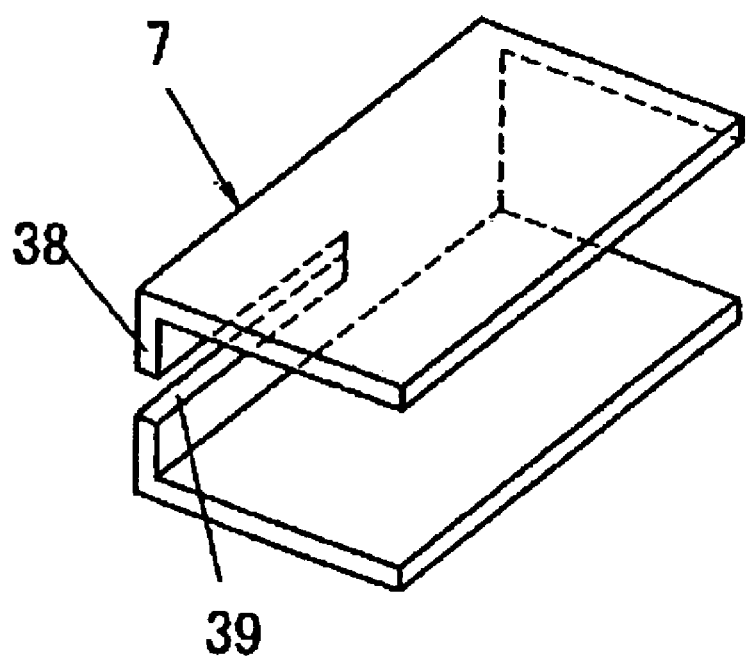

FIG. 10 shows still another embodiment. The basic constitution of this embodiment is the same as the embodiment described above, and common elements are labeled by the same reference numbers and their explanation is not repeated.

This embodiment has expansion prevention module 7 for preventing the blood-constricting cuff band 1 from expanding in the storage position (II). Specifically, the expansion prevention module 7 having a U-shaped cross-section is designed to be mounted from behind the blood-constricting cuff band 1 in the storage position (II). For this purpose, an engaging notch 39 is formed in a back wall 38 of expansion preventing module 7, making it possible to attach the back of the expansion prevention module 7 easily while avoiding parts such as the abovementioned slider 37 for the abovementioned pivot or sliding connection between the blood-constricting cuff band 1 and the sphygmomanometer unit 2. The expansion prevention module 7 may also be combined with the sphygmomanometer unit 2. In this case, the expansion prevention module 7 may be constituted such that it does not hinder the blood-constricting cuff band 1 when changing position.

In this embodiment, the blood-constricting cuff band 1 can be prevented from expanding in the storage position (II) by the expansion prevention module 7, and the sphygmomanometer can be made even thinner.

Figure 11:
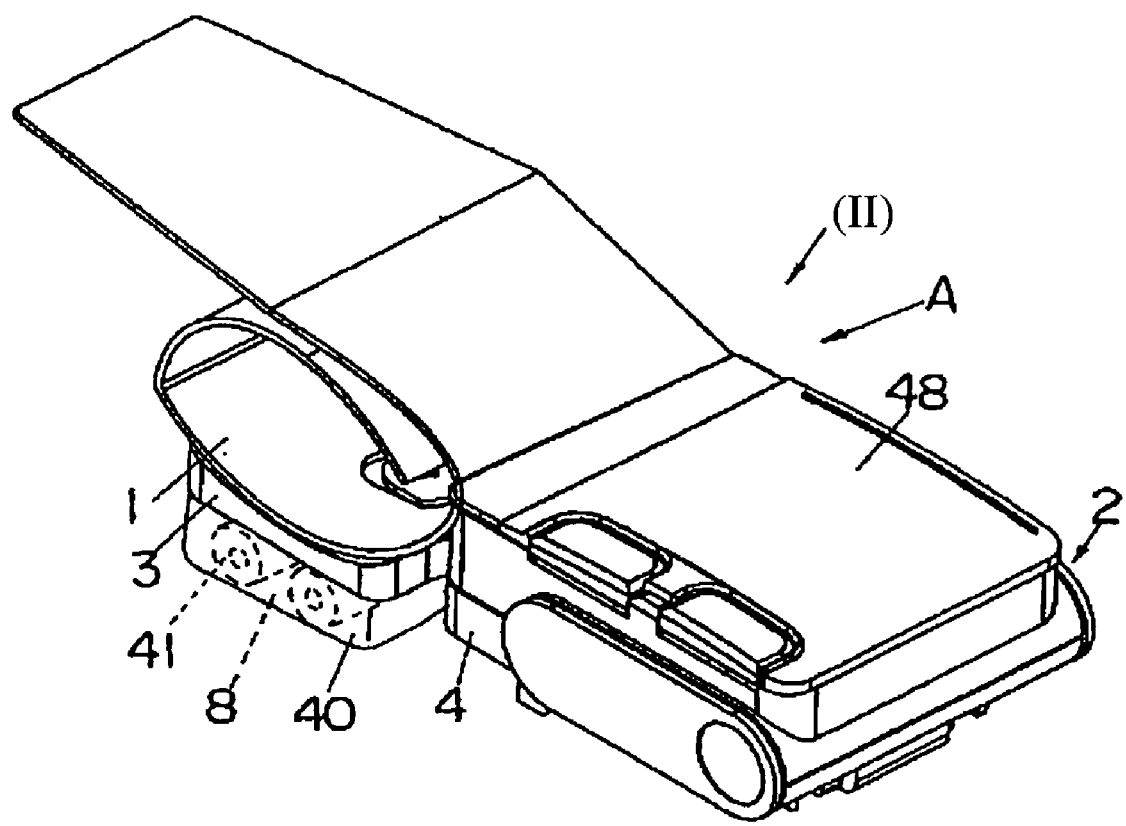
FIG. 11 is a perspective diagram of still another embodiment of the same.

FIG. 11 shows still another embodiment. The basic constitution of this embodiment is the same as the embodiment described above, and common elements are labeled by the same reference numbers and their explanation is not repeated.

In this embodiment, a lid 40 is installed detachably to the connecting base 3 such that the power source battery 41 is stored in the battery storage space 8 above the connecting base 3.

By storing the power source battery 41 in the blood-constricting cuff band 1 in this embodiment, there is no need to create a storage space for the power source battery 41 in the sphygmomanometer unit 2. Thus, sphygmomanometer unit 2 can be made more compact.

Figure 12A:
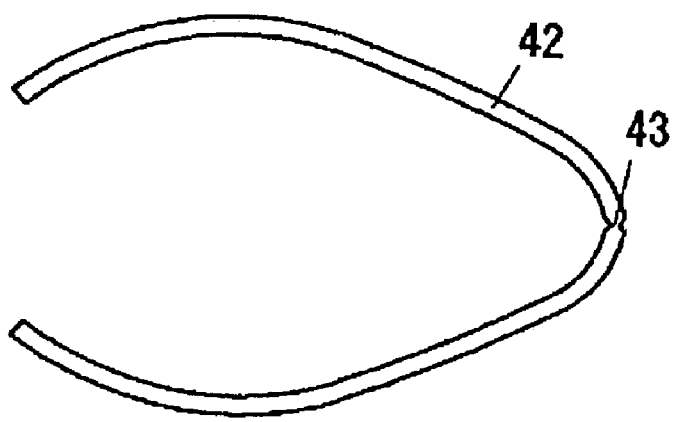
FIG. 12 is a diagram showing still another embodiment of the same, where (a) and (b) are schematic diagrams.
Figure 12B:
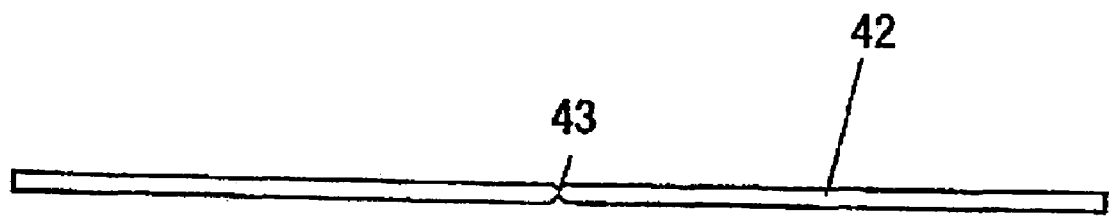

As shown in FIG. 12, Mounting on the wrist may be facilitated by forming a thin part 43 as to a clip plate 42, which is formed in roughly C-shaped, is inserted in the cuff part of the blood-constricting cuff band 1.

FIGS. 13 through 18 show the storage case 27 for storing the sphygmomanometer A described in detail above in the storage position (II).

Figure 13A:
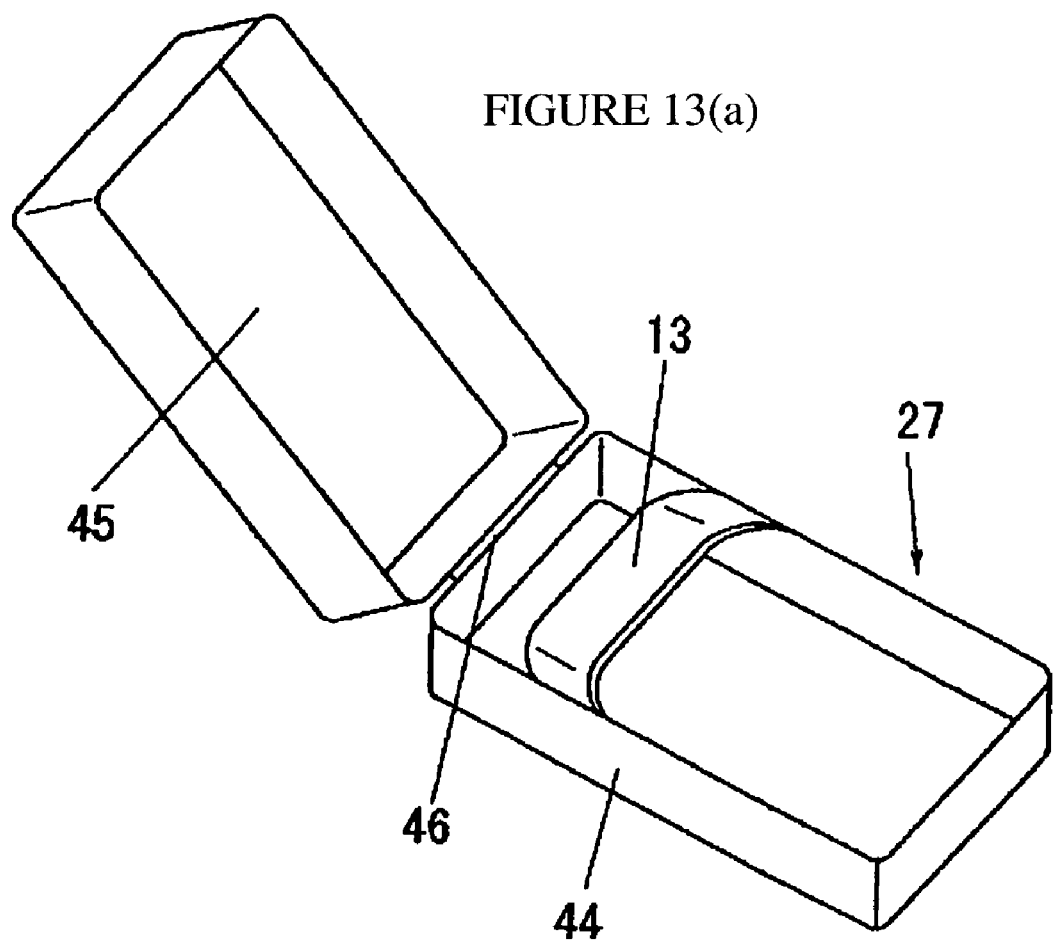
FIG. 13 is a diagram showing a storage case for storing the sphygmomanometer of this invention, where FIG. 13($a$) is a perspective diagram and FIG. 13($b$) is a section showing the storage position.
Figure 13B:
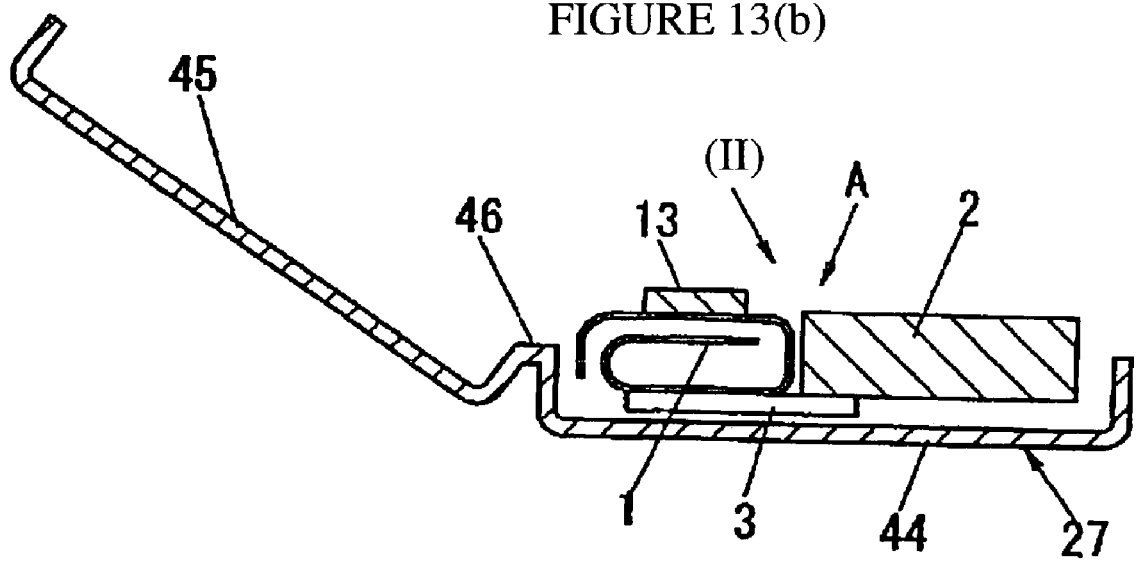

The storage case 27 in the embodiment shown in FIG. 13 is comprised of a case body 44 and a lid 45 connected by the bending part 46, and made, for example, of synthetic resin. The case body 44 is formed with the presser member 13 for preventing the blood-constricting cuff band 1 from expanding in the storage position (II).

In this embodiment, when the sphygmomanometer A is stored in the storage case 27, the blood-constricting cuff band 1 is prevented from expanding in the storage position (II) by the presser member 13, and the storage case 27 can be made thin.

Figure 14A:
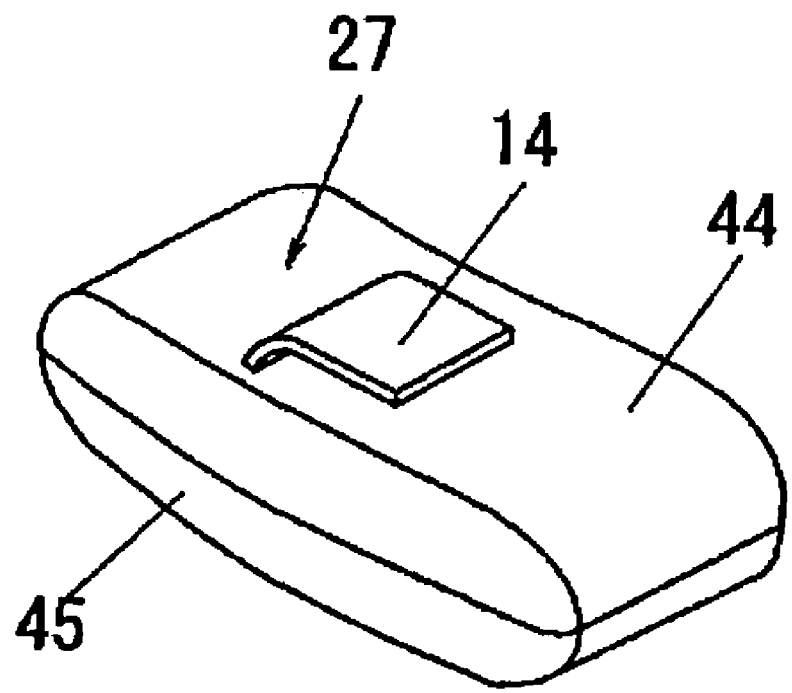
FIG. 14 is a diagram showing another embodiment of the same, where FIG. 14($a$) is a perspective diagram and FIG. 14($b$) is a section.
Figure 14B:
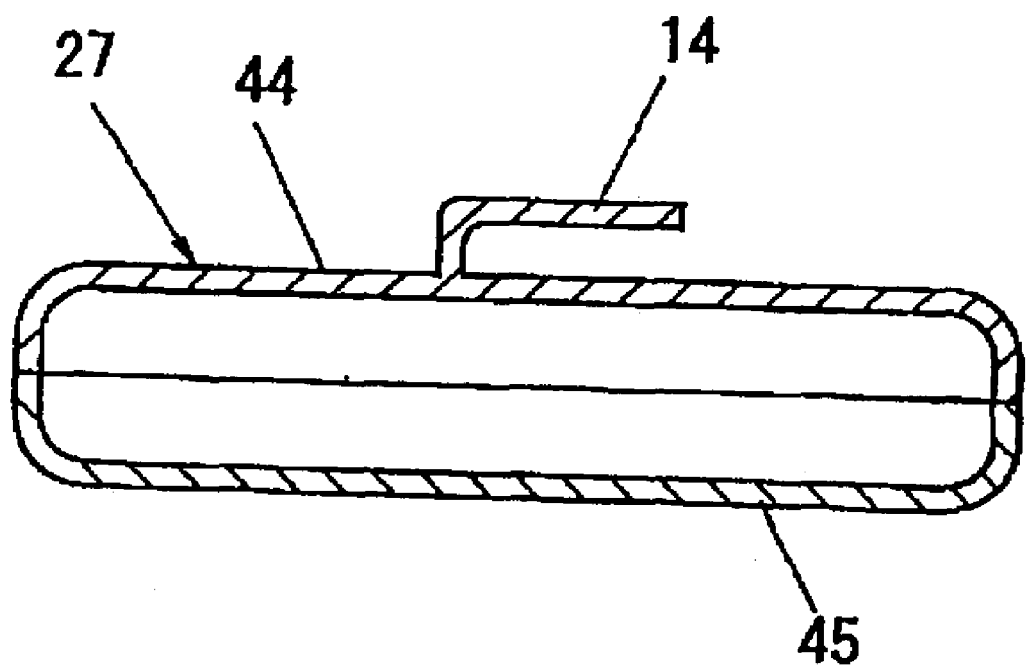

FIG. 14 shows still another embodiment. The basic constitution of this embodiment is the same as the embodiment described above, and common parts are labeled by the same reference numbers and their explanation is not repeated.

In this embodiment, the storage case 27 can be carried easily by installing the latching hook 14 for latching to clothing or the like on the outside of the case and latching the latching hook 14 to a pocket or belt.

Figure 15A:
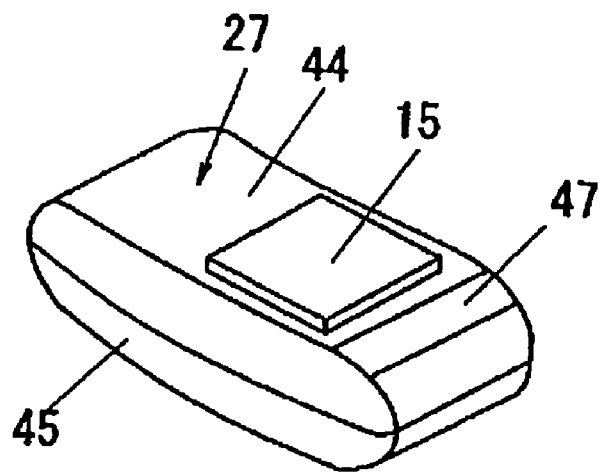
FIG. 15 is a diagram showing still another embodiment of the same, where FIG. 15($a$) is a perspective diagram and FIG. 15($b$) is a schematic diagram.
Figure 15B:
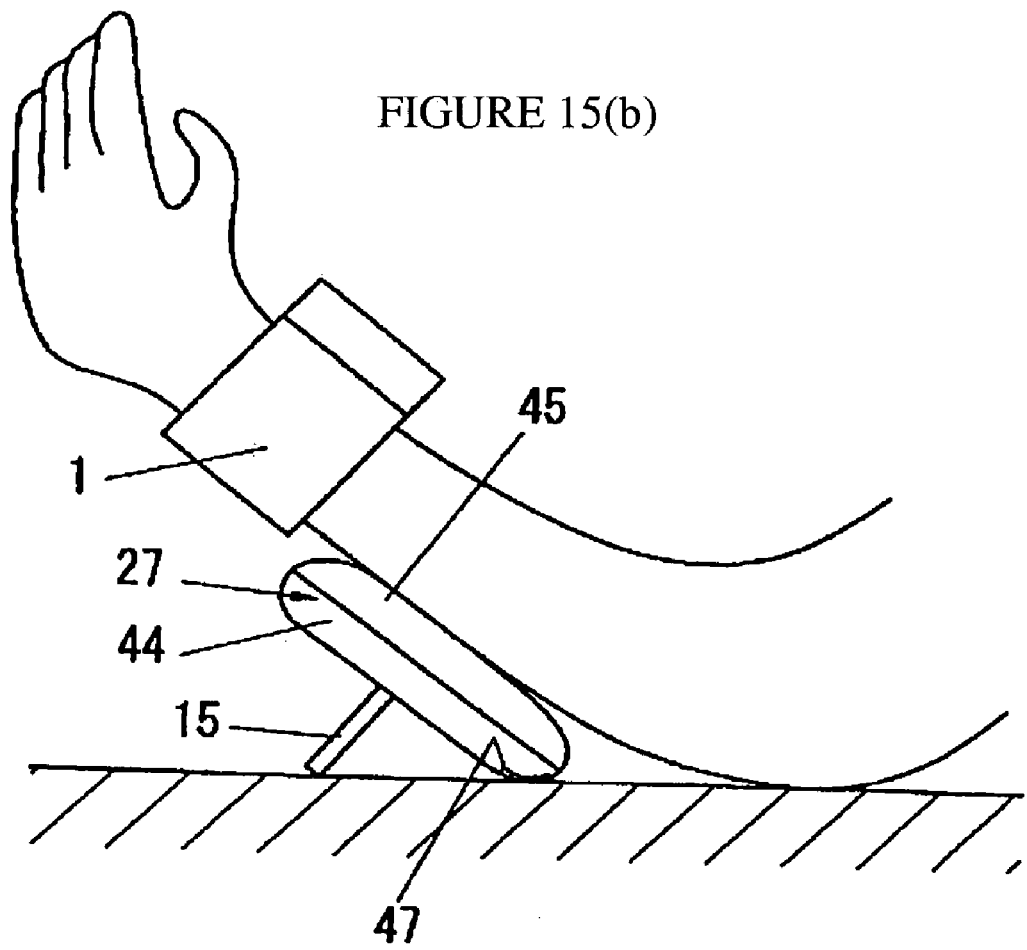

FIG. 15 shows still another embodiment. The basic constitution of this embodiment is the same as the embodiment described above, and common elements are labeled by the same reference numbers and their explanation is not repeated.

In this embodiment, the support leg 15 standing at an angle to the storage case 27 is installed freely rotating on the outside of the case. By standing the support leg 15 up, the storage case 27 can be raised at an angle and act as a wrist stand for the wrist to lean on, enabling stable measurement of blood pressure with the wrist raised to roughly the height of the heart.

Figure 16A:
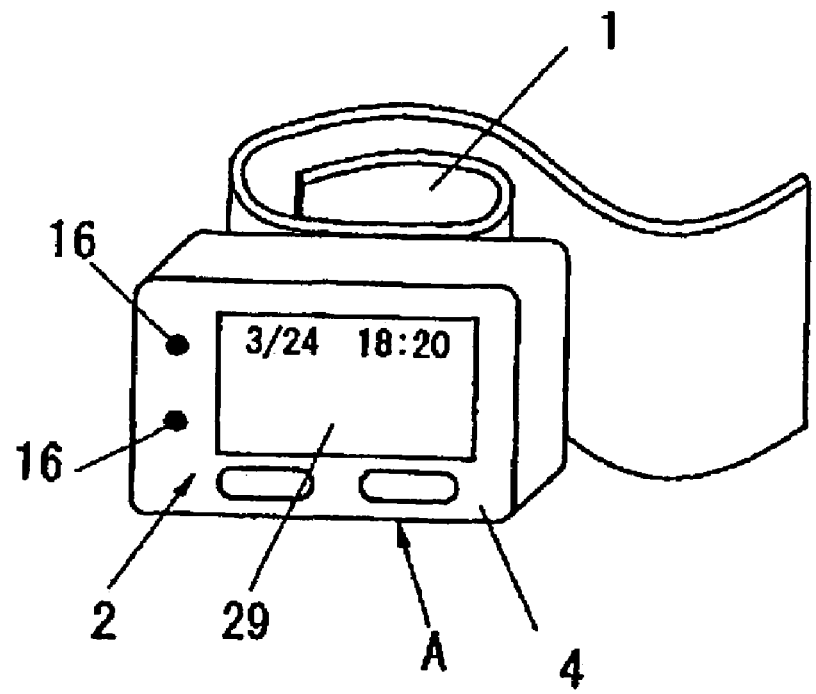
FIG. 16 is a diagram showing still another embodiment of the same, where FIG. 16($a$) and FIG. 16($b$) are schematic diagrams.
Figure 16B:
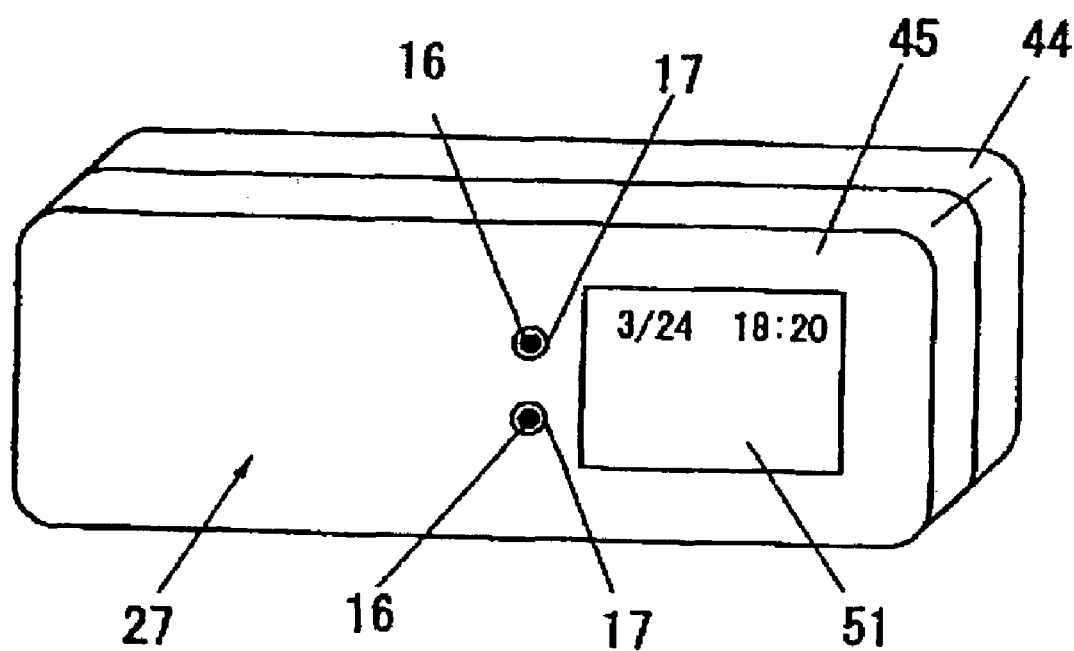

FIG. 16 shows still another embodiment. The basic constitution of this embodiment is the same as the embodiment described above, and common elements are labeled by the same reference numbers and their explanation is not repeated.

In this embodiment, small holes 17 are formed for depressing and operating switches 16 such as calendar and time setting switches on the sphygmomanometer A when stored. The switches 16 such as calendar and time setting switches installed on the sphygmomanometer unit 2 can be operated externally by a stylus through small holes 17. The display window 29 of the sphygmomanometer A can be viewed by installing a transparent window 51 in the storage case 27.

Figure 17A:
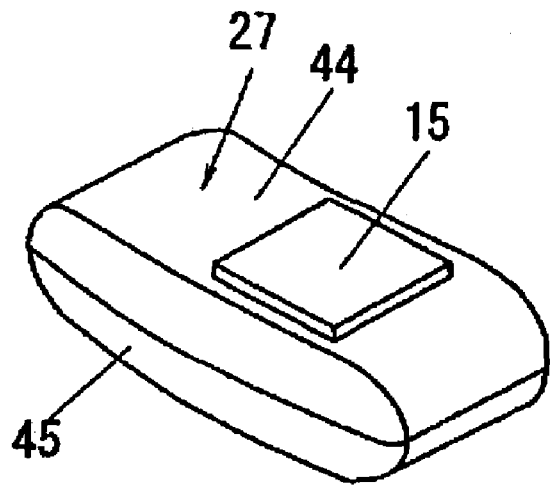
FIG. 17 is a diagram showing still another embodiment of the same, where FIG. 17($a$) is a perspective diagram and FIG. 17($b$) is a schematic diagram.
Figure 17B:
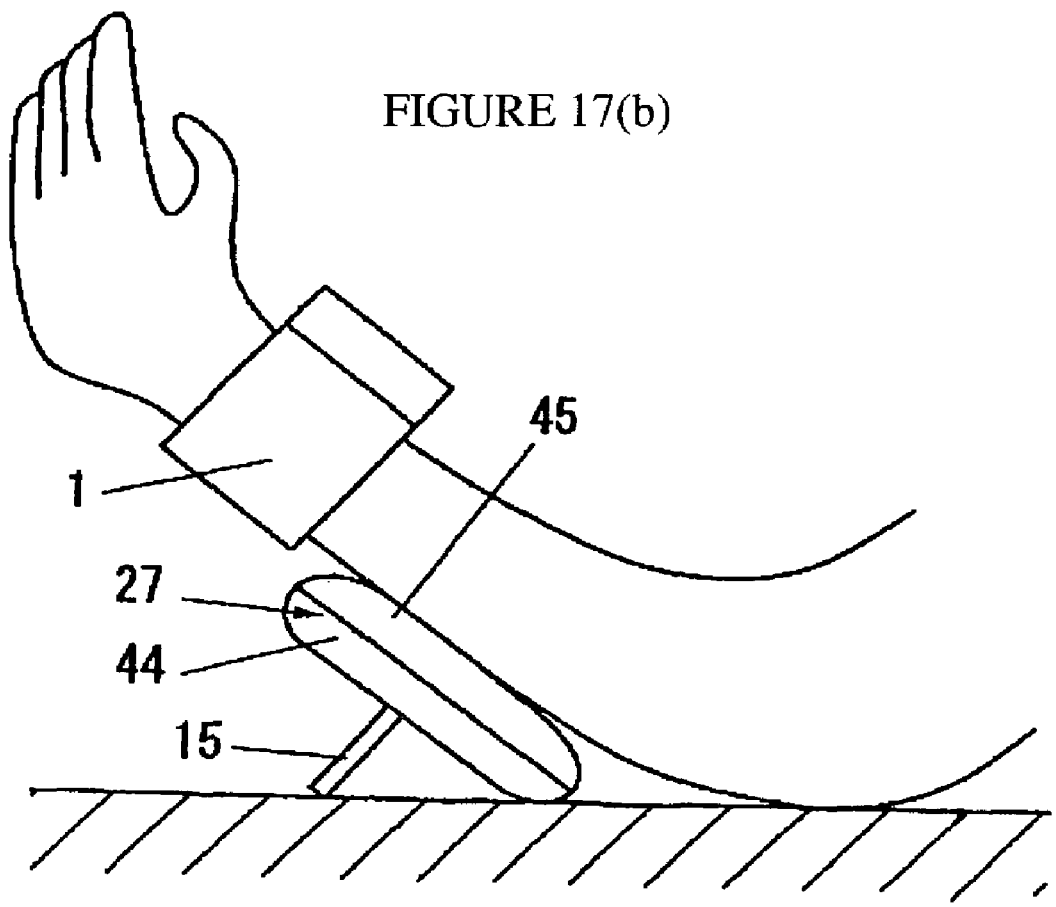

FIG. 17 shows still another embodiment. The basic constitution of this embodiment is the same as the embodiment described above, and common elements are labeled by the same reference numbers and their explanation is not repeated.

In this embodiment, the arm (wrist) can be kept from slipping during measurement by affixing non-slip part 47 made of rubber or synthetic resin to a case body 44.

Figure 18:
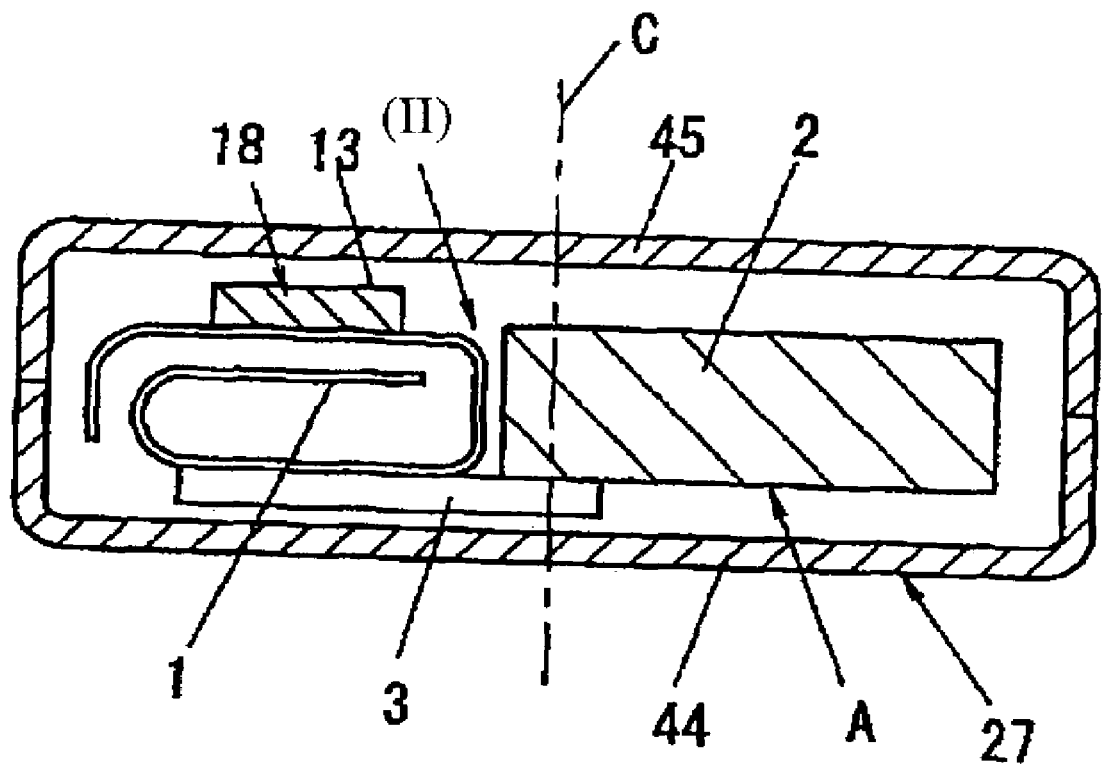
FIG. 18 is a section of still another embodiment of the same.

FIG. 18 shows still another embodiment. The basic constitution of this embodiment is the same as the embodiment described above, and common elements are labeled by the same reference numbers and their explanation is not repeated.

This embodiment has module 18 for balancing the weight of the blood-constricting cuff band 1 and the sphygmomanometer unit 2 of the sphygmomanometer A on either side of center-line C when stored. Specifically, the sphygmomanometer A is kept stable when carrying and prevented from falling or the like by making the presser member 13 of metal and balancing the weight of the sphygmomanometer A to the left and right in the storage position (II).

In one or more embodiments, the invention is the sphygmomanometer combining the blood-constricting cuff band with the sphygmomanometer unit, and constitutes a structure that can be switched between the measurement position with the sphygmomanometer unit overlapping the blood-constricting cuff band and the storage position with the blood-constricting cuff band and the sphygmomanometer unit placed side by side. As a result, this invention has the advantage that the sphygmomanometer can be switched to the storage position with the blood-constricting cuff band and the sphygmomanometer unit placed side by side, and the sphygmomanometer combining the blood-constricting cuff band with the sphygmomanometer unit can be made compact, facilitating carrying and the like.

In one or more embodiments of the invention, the blood-constricting cuff band is pivoted freely rotating on the pivot shaft of the unit case of the sphygmomanometer unit, and the pivot shaft functions as a sort of air pipe for supplying and expelling air from the sphygmomanometer unit to the blood-constricting cuff band. As a result, this invention has the advantage that the blood-constricting cuff band can be placed side by side with the sphygmomanometer unit by rotating the blood-constricting cuff band on the pivot shaft, making the sphygmomanometer even thinner, and because the pivot shaft functions as a sort of air pipe, the air supply system can be simplified rather than complicated.

In one or more embodiments, the invention has an air supply/stop module for enabling air supply from the sphygmomanometer unit to the blood-constricting cuff band when in measurement position and disabling air supply from the sphygmomanometer unit to the blood-constricting cuff band 1 when in the storage position. As a result, this invention has the advantage that the blood-constricting cuff band cannot be supplied air by the air supply/stop module when it is in the storage position, preventing it from operating when not engaged in measurement.

In one or more embodiments of the invention, the blood-constricting cuff band is constituted sliding freely to the sphygmomanometer unit. As a result, this has the advantage that the constitution for placing the blood-constricting cuff band in storage position can be easily simplified compared to a rotating constitution.

In one or more embodiments, the invention has an expansion prevention module for preventing the blood-constricting cuff band from expanding in storage position. As a result, this has the advantage that the blood-constricting cuff band can be prevented from expanding by the expansion prevention module, and the sphygmomanometer can be made even thinner.

In one or more embodiments of the invention, the blood-constricting cuff band is held on a connecting base of a hard substance, and the connecting base is pivoted on the unit case of the sphygmomanometer unit. As a result, this invention has the advantage that the blood-constricting cuff band can be switched between measurement position and storage position and held stably in each position by way of a connecting base of a hard substance.

In one or more embodiments of the invention, the tube aperture on both ends is formed on the side of the connecting base toward the unit case, connecting pipes are extended perpendicular to the axial center of the tubular pivot shafts inserted into both ends of the tube, one end of each tubular pivot shaft is closed, the polygonal shaft having parallel faces is formed on this closed end, a square bearing for receiving the parallel faces of the polygonal shaft is formed on the unit case to hold the pivot shaft and stop it from rotating, tubular pivot shafts are connected freely rotating in the tube by inserting the pivot shafts through O-rings onto both ends of the tube, and the air pipe from the pump is connected to the connecting pipe of the pivot shaft. As a result, this invention has the advantage that the shafts can be sealed by O-rings, the polygonal shafts of the pivot shafts can be inserted unable to rotate in the square bearings, the pivot shafts can be held securely while facilitating assembly of the pivot shafts with the unit case, and rotation of the connecting base can be stabilized. Moreover, the different rotating angles can be selected for the polygonal shafts and the different direction can be selected for the connecting pipes extending from the pivot shafts, producing a variety of potential placements for parts of the sphygmomanometer unit such as the pump.

In one or more embodiments of the invention, the hook is formed on either the unit case or the connecting base, and the hook catch is formed on the other one for catching the hook to hold the blood-constricting cuff band in measurement position. As a result, this has the advantage that the connecting base can be fixed to the unit case and the blood-constricting cuff band can be held stably in the measurement position by catching the hook by the hook catch.

In one or more embodiments of the invention, the battery storage space is formed on the connecting base. As a result, this has the advantage that a battery storage space need not be installed on the sphygmomanometer unit, simplifying the constitution of the sphygmomanometer unit.

In one or more embodiments of the invention, the switch is installed for switching the power source battery off only when the blood-constricting cuff band is in storage position. As a result, this invention has the advantage that the switch cannot be switched on when the blood-constricting cuff band is in storage position, preventing unexpected consumption of power.

In one or more embodiments of the invention, the switch is installed for switching the power source on only when the blood-constricting cuff band is in measurement position. As a result, this invention has the advantage that the switch cannot be switched on except when the blood-constricting cuff band is in measurement position, preventing unexpected consumption of power.

In one or more embodiments, the invention is a storage case for storing the sphygmomanometer in the storage position, and has a presser member for preventing the blood-constricting cuff band from expanding. As a result, this invention has the advantage that the blood-constricting cuff band is pressed by the presser piece in storage position and prevented from expanding when the sphygmomanometer is stored in the storage case, and the storage case can be made thin.

In one or more embodiments of the invention, the latching hook is installed on the outside of the case for latching to clothing or the like. As a result, this invention has the advantage that the storage case can be easily carried by fastening the fastener hook to a pocket or belt.

In one or more embodiments of the invention, the support leg standing at an angle to the storage case is installed freely rotating on the outside of the case. As a result, this invention has the advantage that the storage case can be raised at an angle by standing the support leg up, enabling stable measurement of blood pressure with the wrist raised to roughly the height of the heart.

In one or more embodiments of the invention, the small hole is formed for depressing and operating the switch on the sphygmomanometer when stored. As a result, this invention has the advantage that the switch such as a time setting switch installed on the sphygmomanometer unit can be operated externally through the small hole.

In one or more embodiments, the invention has a module for balancing the weight of the blood-constricting cuff band and the sphygmomanometer unit of the sphygmomanometer on either side of the center-line when stored. As a result, this invention has the advantage that the sphygmomanometer can be stabilized when carried, preventing dropping.

What is claimed is:

1. A sphygmomanometer combining a blood-constricting cuff band with a sphygmomanometer unit having structure to measure blood pressure, where the sphygmomanometer unit comprises a box-shaped body having a top surface, a bottom surface, and a plurality of side surfaces;
    wherein the blood-constricting cuff band and the body are rotatably connected via a pivot such that the body and cuff may be switched between a measurement position, in which the blood-constricting cuff is positioned adjacent to the bottom surface of the sphygmomanometer unit, and
    a storage position, in which the blood-constricting cuff band is positioned adjacent to one of the plurality of side surfaces of the sphygmomanometer unit, whereby the sphygmomanometer unit and the blood-constricting unit are positioned in a side-by-side configuration, and and wherein the blood-constricting cuff band is external to the body.

2. The sphygmomanometer described in claim 1, comprising an air supply/stop module for enabling air supply from the sphygmomanometer unit to the blood-constricting cuff band when in the measurement position and disabling air supply from the sphygmomanometer unit to the blood-constricting cuff band when in the storage position.

3. The sphygmomanometer described in claim 1, comprising an expansion prevention module for preventing the blood-constricting cuff band from expanding in the storage position.

4. A sphygmomanometer combining a blood-constricting cuff band with a sphygmomanometer unit, comprising a structure that can be switched between a measurement position with the sphygmomanometer unit overlapping the blood-constricting cuff band and a storage position with the blood-constricting cuff band and the sphygmomanometer unit placed side by side, wherein the blood-constricting cuff band freely rotates on a pivot shaft of a unit case of the sphygmomanometer unit, and the pivot shaft serves as an air pipe for supplying and expelling air from the sphygmomanometer unit to the blood-constricting cuff band.

5. The sphygmomanometer described in claim 4, wherein the blood-constricting cuff band is held by a connecting base connected pivotally to the unit case of the sphygmomanometer unit.

6. The sphygmomanometer described in claim 5, comprising a tube formed on an end of the connecting base, a connecting pipe extending perpendicular to the axial center of the pivot shaft inserted into an end of the tube, a polygonal shaft having flat faces formed on an end of the pivot shaft, and a polygonal bearing for receiving the flat faces of the polygonal shaft.

7. The sphygmomanometer described in claim 5, comprising a hook formed either on the unit case or the connecting base, and forming a hook catch on the other one for catching the hook to hold the blood-constricting cuff band in the measurement position.

8. The sphygmomanometer described in claim 5, comprising a battery storage space formed on the connecting base.

9. The sphygmomanometer described in claim 5, comprising an installed switch for switching the power source battery off only when the blood-constricting cuff band is in the storage position.

10. The sphygmomanometer described in claim 5, an installed switch for switching the power source on only when the blood-constricting cuff band is in the measurement position.

11. A sphygmomanometer, comprising:

a sphygmomanometer unit having structure to measure blood pressure;

a blood-constricting cuff band, wherein the blood constricting cuff band is external to the sphygmomanometer unit; and a connecting mechanism pivotally connecting the sphygmomanometer unit with the blood-constricting cuff band, wherein the connecting mechanism is configured to switch between a measurement position such that the blood-constricting cuff is positioned adjacent to a bottom surface of the sphygmomanometer unit and a storage position such that the blood-constricting cuff is positioned adjacent to a side surface of the sphygmomanometer unit, whereby the blood-constricting cuff and the sphygmomanometer form a side-by-side configuration.

12. The sphygmomanometer described in claim 11, wherein the connecting mechanism comprising:

a connecting base configured to hold the blood-constricting cuff band; and a pivot shaft pivotally connecting the connecting base.

13. A sphygmomanometer, comprising:

a sphygmomanometer unit;

a blood-constricting cuff band; and a connecting mechanism connecting the sphygmomanometer unit with the blood-constricting cuff, wherein the connecting mechanism comprises a connecting base configured to hold the blood-constricting cuff band and a pivot shaft pivotally connecting the connecting base, thereby the connecting mechanism is configured to switch between a measurement position with the sphygmomanometer unit overlapping the blood-constricting cuff band and a storage position with the sphygmomanometer unit and the blood-constricting cuff band placed side by side, and wherein the pivot shaft is configured to serve as an air pipe to supply air from a pump and expel the air.

* * * * *